US011948284B2

(12) United States Patent
Song et al.

(10) Patent No.: US 11,948,284 B2
(45) Date of Patent: Apr. 2, 2024

(54) 3D MODELING METHOD FOR PORE-FILLING HYDRATE SEDIMENT BASED ON CT IMAGE

(71) Applicant: DALIAN UNIVERSITY OF TECHNOLOGY, Liaoning (CN)

(72) Inventors: Yongchen Song, Liaoning (CN); Yanghui Li, Liaoning (CN); Peng Wu, Liaoning (CN); Xiang Sun, Liaoning (CN); Weiguo Liu, Liaoning (CN); Jiafei Zhao, Liaoning (CN); Mingjun Yang, Liaoning (CN); Lei Yang, Liaoning (CN); Zheng Ling, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 421 days.

(21) Appl. No.: 17/416,028

(22) PCT Filed: Jul. 23, 2020

(86) PCT No.: PCT/CN2020/103682
§ 371 (c)(1),
(2) Date: Jun. 18, 2021

(87) PCT Pub. No.: WO2022/000628
PCT Pub. Date: Jan. 6, 2022

(65) Prior Publication Data
US 2022/0156901 A1     May 19, 2022

(30) Foreign Application Priority Data
Jul. 3, 2020   (CN) .......................... 202010629561.3

(51) Int. Cl.
*G06T 7/136*   (2017.01)
*G01N 23/046*  (2018.01)
(Continued)

(52) U.S. Cl.
CPC ............. *G06T 5/30* (2013.01); *G01N 23/046* (2013.01); *G06T 7/11* (2017.01); *G06T 7/136* (2017.01);
(Continued)

(58) Field of Classification Search
CPC ....... G01N 2223/419; G01N 2223/616; G01N 23/046; G01N 33/241; G06T 17/00;
(Continued)

(56) References Cited

U.S. PATENT DOCUMENTS 8,909,508 B2 * 12/2014 Hurley .................... G06T 7/11
                                                         703/10
9,134,457 B2 *  9/2015 Hurley .................. G01V 20/00
(Continued)

FOREIGN PATENT DOCUMENTS

CN    102323305 A    1/2012
CN    106290537 A    1/2017
(Continued)

OTHER PUBLICATIONS

Zhu, Qin, "Study on Highly Selective Detection of Amino Acids by Using Ultrastructure Metal Nanocomposite Membranes", (Engineering Technology I, China Master's Theses Full-Text Database), No. No. 07, Jul. 15, 2020 (Jul. 15, 2020), ISSN:1674-0246, p. 27, line 1—p. 37, bottom line. (pp. 85).
(Continued)

*Primary Examiner* — Tsung Yin Tsai
(74) *Attorney, Agent, or Firm* — Muncy, Geissler, Olds & Lowe, P.C.

(57) ABSTRACT

The present invention belongs to the technical field of petroleum exploitation engineering, and discloses a 3D modeling method for pore-filling hydrate sediment based on a CT image. Indoor remolding rock cores or in situ site rock cores without hydrate can be scanned by CT; a sediment
(Continued)

Digital Rock Core Image

Sediment Matrix Image Stack

Binarization Segmentation

Pore Image Stack matrix image stack and a pore image stack are obtained by gray threshold segmentation; then, a series of pore-filling hydrate image stacks with different saturations are constructed through image morphological processing of the pore image stack such as erosion, dilation and image subtraction operation; and a series of digital rock core image stacks of the pore-filling hydrate sediment with different saturations are formed through image subtraction operation and splicing operation to provide a relatively real 3D model for the numerical simulation work of the basic physical properties of a reservoir of natural gas hydrate.

1 Claim, 3 Drawing Sheets

(51) Int. Cl.
*G06T 5/30* (2006.01)
*G06T 7/11* (2017.01)
*G06T 17/00* (2006.01)

(52) U.S. Cl.
CPC .... *G06T 17/00* (2013.01); *G06T 2207/10081* (2013.01)

(58) Field of Classification Search
CPC ......... G06T 17/005; G06T 2207/10081; G06T 2207/30108; G06T 5/30; G06T 7/0004; G06T 7/11; G06T 7/136; G06T 7/155
See application file for complete search history.

(56) References Cited

U.S. PATENT DOCUMENTS

| | | | |
|---|---|---|---|
| 10,061,061 B2* | 8/2018 | Ziauddin | E21B 43/25 |
| 10,508,997 B1* | 12/2019 | Lee | G06T 7/246 |
| 2012/0221306 A1* | 8/2012 | Hurley | G01V 20/00 |
| | | | 703/6 |
| 2012/0275658 A1* | 11/2012 | Hurley | G06T 7/11 |
| | | | 382/109 |
| 2016/0025895 A1* | 1/2016 | Ziauddin | G01V 20/00 |
| | | | 702/11 |
| 2018/0024262 A1* | 1/2018 | Madof | G01V 99/00 |
| | | | 175/50 |
| 2019/0360948 A1* | 11/2019 | Lee | G01N 33/24 |
| 2022/0230326 A1* | 7/2022 | Song | G06T 17/10 |

FOREIGN PATENT DOCUMENTS

| | | |
|---|---|---|
| CN | 108362815 A | 8/2018 |
| CN | 110082413 A | 8/2019 |
| CN | 110887881 A | 3/2020 |
| WO | WO0242771 A2 | 5/2002 |
| WO | WO-2016007170 A1 * | 1/2016 ........... G01N 15/082 |

OTHER PUBLICATIONS

Li, Yuqing et al., "Graphene Oxide/Triangular Gold Nanoplates/Nafion Composite Modified Electrode Used for Sensitive Detection of L-Tryptophan",(Chemical Journal of Chinese Universities),vol. 39, No. 04, Mar. 22, 2018 (Mar. 22, 2018), p. 637, line 39—p. 642, line 21. (pp. 9).

* cited by examiner

3D MODELING METHOD FOR PORE-FILLING HYDRATE SEDIMENT BASED ON CT IMAGE

TECHNICAL FIELD

The present invention belongs to the technical field of petroleum exploitation engineering, and relates to a modeling method for generating pore-filling hydrate sediment in a 3D digital rock core.

BACKGROUND

Natural gas hydrate is clean energy with abundant reserves and is widely distributed undersea and in permafrost in a cementing type or a pore-filling type. It is estimated that the resources of the natural gas hydrate are twice the total reserves of known coal, petroleum and conventional natural gas, and more than 10 times the total amount of all of the global conventional natural gas.

At present, China, India, Korea, Japan and the like have delineated the hydrate development prospect areas, formulated corresponding development plans, and carried out massive research on basic physical properties of hydrate-bearing sediment such as seepage, heat conduction, electricity conduction and mechanics. However, it is difficult and costly to take the core under pressure in the reservoir of the natural gas hydrate, and the hydrate is disturbed and decomposed in the process of sample transfer. Meanwhile, remolding of indoor hydrate samples cannot accurately control the occurrence type and saturation of the hydrate, and experimental repeatability is poor. In contrast, if 3D digital rock cores (the cementing type and the pore-filling type) close to the in situ reservoir structure can be obtained through a numerical simulation method and relevant numerical analysis of the basic physical properties is conducted, the experimental cost of the hydrate will be reduced obviously and the experimental repeatability is good; and the basic physical properties of the hydrate reservoir are rapidly and accurately evaluated.

The present invention relates to a 3D modeling method for pore-filling hydrate sediment based on a CT image. Remolding or in situ rock cores without the natural gas hydrate are scanned by CT; a series of digital rock core image stacks of pore-filling type natural gas hydrate sediment with different saturations are constructed through image morphological calculation to provide a relatively real 3D numerical model for the numerical simulation analysis of the basic physical properties of the reservoir of the natural gas hydrate.

SUMMARY

The main purpose of the present invention is to propose a 3D modeling method for pore-filling hydrate sediment based on a CT image to provide a relatively real 3D numerical model for the numerical simulation analysis of the basic physical properties of the reservoir of the natural gas hydrate.

The technical solution of the present invention is as follows:
step 1, scanning remolding or in situ rock cores without natural gas hydrate by CT to obtain digital rock core image stacks;
step 2, adjusting the gray threshold of the digital rock core image stacks, conducting binarization segmentation to obtain a sediment matrix and a pore, and respectively saving as the image stacks;
step 3, firstly eroding a pore image stack obtained in step 2 at x pixel and then dilating at x pixel to obtain a pore-filling hydrate image stack;
step 4, performing image subtraction; and subtracting the pore-filling hydrate image stack obtained in step 3 from the pore image stack obtained in step 2 to obtain a new pore image stack corresponding to the pore-filling hydrate image stack obtained in step 3;
step 5, splicing and combining the sediment matrix image stack obtained in step 2, the pore-filling hydrate image stack obtained in step 3 and the new pore image stack obtained in step 4 to form a digital rock core image stack with the sediment matrix, the pore-filling hydrate and the pore, which is the digital rock core image stack of the pore-filling hydrate sediment;
step 6, repeatedly executing step 3 to step 5, and adjusting x value to obtain the digital rock core image stacks of the pore-filling hydrate sediment with different hydrate saturations.

The present invention has the beneficial effects that: a series of digital rock core image stacks of pore-filling hydrate sediment with different saturations can be constructed based on the remolding or in situ rock cores without the natural gas hydrate through image morphological calculation to provide the relatively real 3D numerical model for the numerical simulation analysis of the basic physical properties of the hydrate reservoir. The experimental cost of the hydrate is reduced obviously and the experimental repeatability is good; and the basic physical properties of the hydrate reservoir are rapidly and accurately evaluated.

DETAILED DESCRIPTION

Specific embodiments of the present invention are further described below in combination with accompanying drawings and the technical solution.

Embodiments

Figure 1:
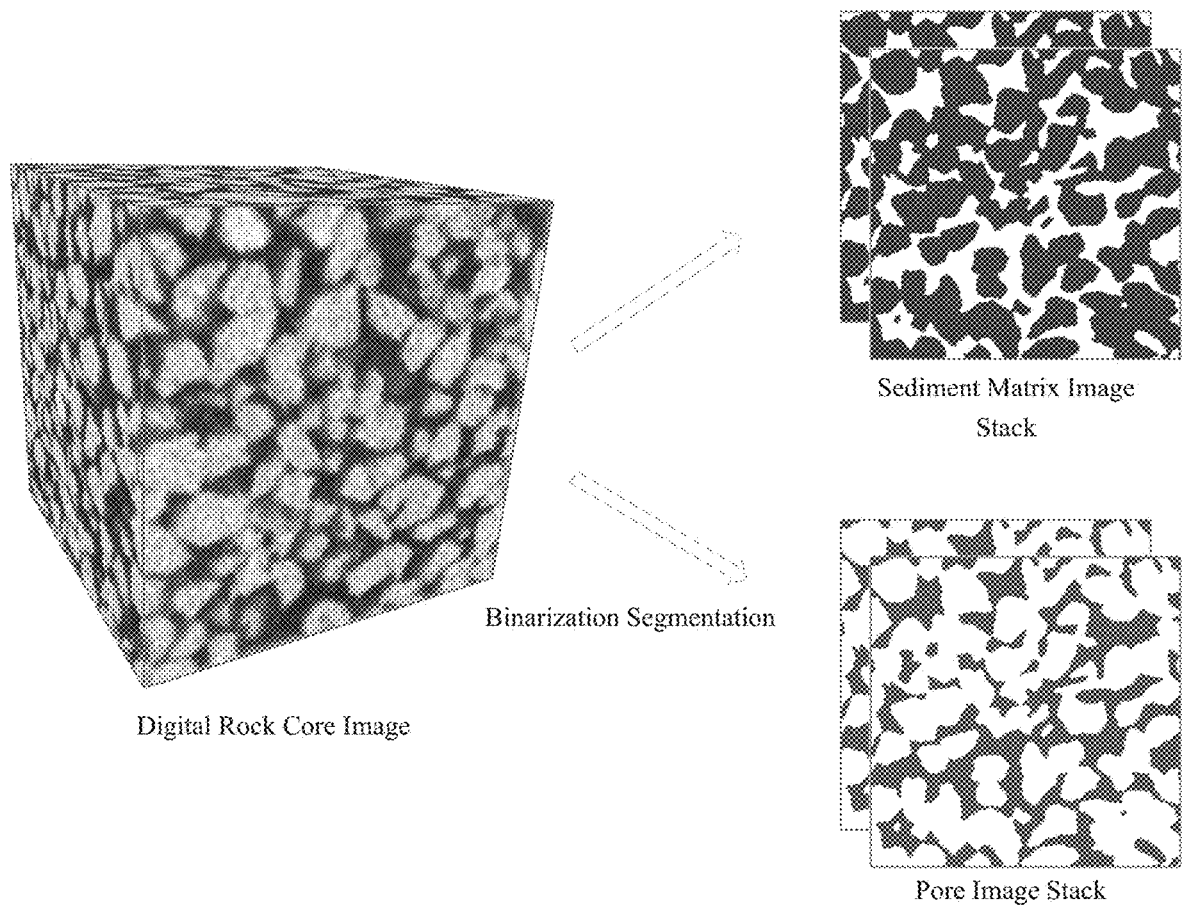
FIG. 1 shows the binarization results of sediment matrices and pores.
Figure 2:
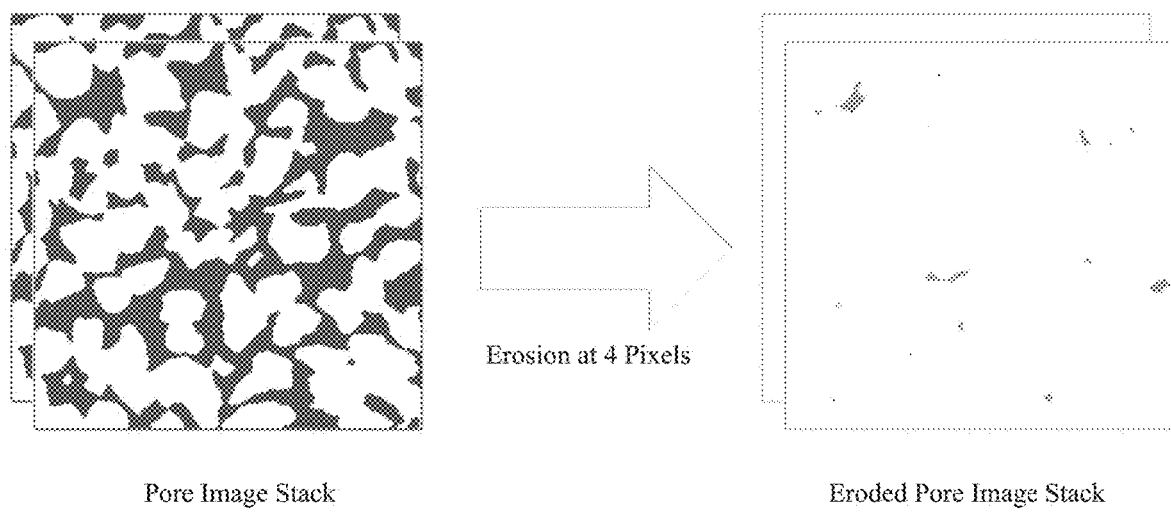
FIG. 2 is a schematic diagram of image erosion at 4 pixels.
Figure 3:
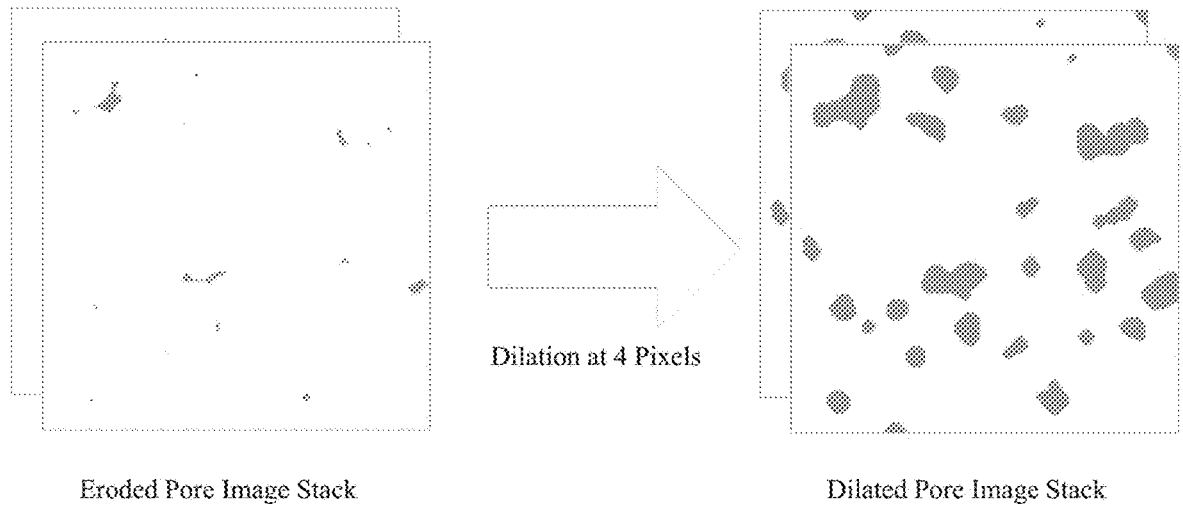
FIG. 3 is a schematic diagram of image dilation at 4 pixels.
Figure 4:
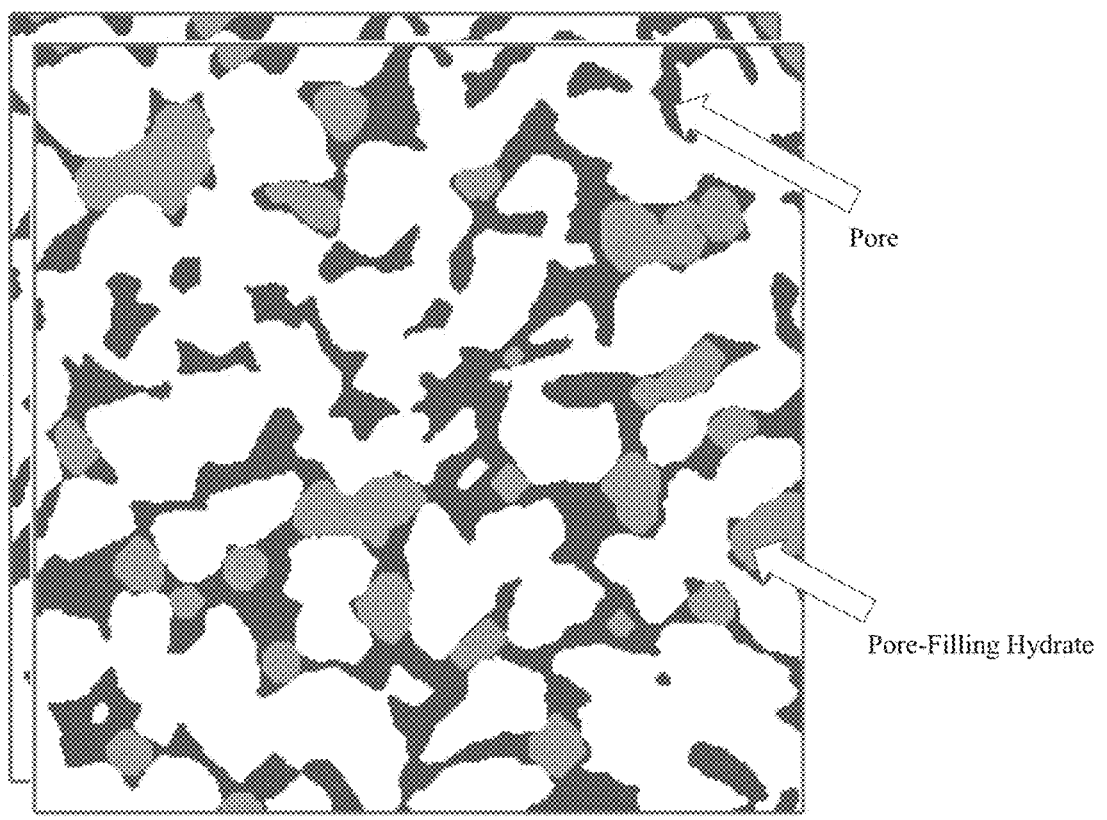
FIG. 4 shows the result of image subtraction.
Figure 5:
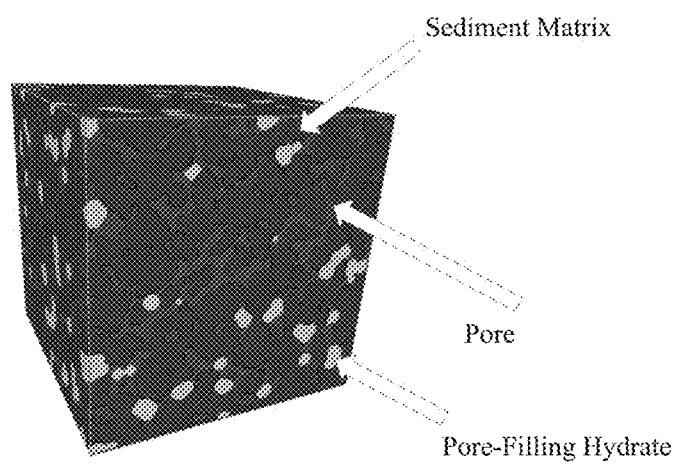
FIG. 5 shows a digital rock core image stack of pore-filling hydrate sediment.

A 3D modeling method for pore-filling hydrate sediment based on a CT image comprises the following steps:
step 1, scanning remolding rock cores (particle size distribution: 0.01-1 mm; median particle size: 0.15 mm; porosity: 41%) without natural gas hydrate by CT to obtain digital rock core image stacks (resolution: 1024*1024; voxel size: 0.004 mm);
step 2, adjusting the gray threshold of the digital rock core image stacks, conducting binarization segmentation to obtain a sediment matrix and a pore, and respectively saving as the image stacks, as shown in FIG. 1;
step 3, firstly eroding a pore image stack obtained in step 2 at 4 pixels, as shown in FIG. 2, and then dilating at 4 pixels, as shown in FIG. 3, to obtain a pore-filling hydrate image stack;

step 4, performing image subtraction; and subtracting the pore-filling hydrate image stack obtained in step 3 from the pore image stack obtained in step 2 to obtain a new pore image stack corresponding to the pore-filling hydrate image stack obtained in step 3, as shown in FIG. 4;

step 5, splicing and combining the sediment matrix image stack obtained in step 2, the pore-filling hydrate image stack obtained in step 3 and the new pore image stack obtained in step 4 to form a digital rock core image stack with the sediment matrix, the pore-filling hydrate and the pore, which is the digital rock core image stack of the pore-filling hydrate sediment (saturation: 28.5%), as shown in FIG. 5.

The invention claimed is:

1. A 3D modeling method for pore-filling hydrate sediment based on CT image, comprising steps of:

step 1, scanning remolding or in situ rock cores without natural gas hydrate by CT to obtain digital rock core image stacks;

step 2, adjusting the gray threshold of the digital rock core image stacks, conducting binarization segmentation to obtain a sediment matrix and a pore, and respectively saving as the image stacks;

step 3, firstly eroding a pore image stack obtained in step 2 at x pixel and then dilating at x pixel to obtain a pore-filling hydrate image stack;

step 4, performing image subtraction; and subtracting the pore-filling hydrate image stack obtained in step 3 from the pore image stack obtained in step 2 to obtain a new pore image stack corresponding to the pore-filling hydrate image stack obtained in step 3;

step 5, splicing and combining the sediment matrix image stack obtained in step 2, the pore-filling hydrate image stack obtained in step 3 and the new pore image stack obtained in step 4 to form a digital rock core image stack with the sediment matrix, the pore-filling hydrate and the pore, which is the digital rock core image stack of the pore-filling hydrate sediment;

step 6, repeatedly executing step 3 to step 5, and adjusting x value to obtain the digital rock core image stacks of the pore-filling hydrate sediment with different hydrate saturations.

* * * * *